United States Patent [19]

Wada

[11] 4,304,468
[45] Dec. 8, 1981

[54] EYE REFRACTOMETER HAVING A VIEWING TARGET PROJECTING SYSTEM

[75] Inventor: Shinji Wada, Tokyo, Japan
[73] Assignee: Tokyo Kogaru Kikai Kabushiki Kaisha, Tokyo, Japan
[21] Appl. No.: 150,205
[22] Filed: May 15, 1980
[30] Foreign Application Priority Data
May 21, 1979 [JP] Japan .................................. 54-62360
[51] Int. Cl.³ .............................................. A61B 3/10
[52] U.S. Cl. ....................................... 351/13; 351/14; 351/16
[58] Field of Search .......................... 351/7, 13, 14, 16
[56] References Cited
U.S. PATENT DOCUMENTS
4,021,102  5/1977  Iizuka ..................................... 351/13

Primary Examiner—John K. Corbin
Assistant Examiner—Rodney B. Bovernick
Attorney, Agent, or Firm—Brumbaugh, Graves, Donohue & Raymond

[57] ABSTRACT

An eye refractometer including a measuring target projecting optical system for projecting a measuring target to a patient's eye using an infrared ray. A viewing target is provided in the projecting system and located more distant from the patient's eye than the measuring target. A filter is located between the two targets and has a portion which is transparent to visible light and corresponds to the viewing target. The remainder of the filter is opaque to the visible light but transparent to infrared ray. The two targets and the filter are assembled together so that they are moved as a unit.

5 Claims, 2 Drawing Figures

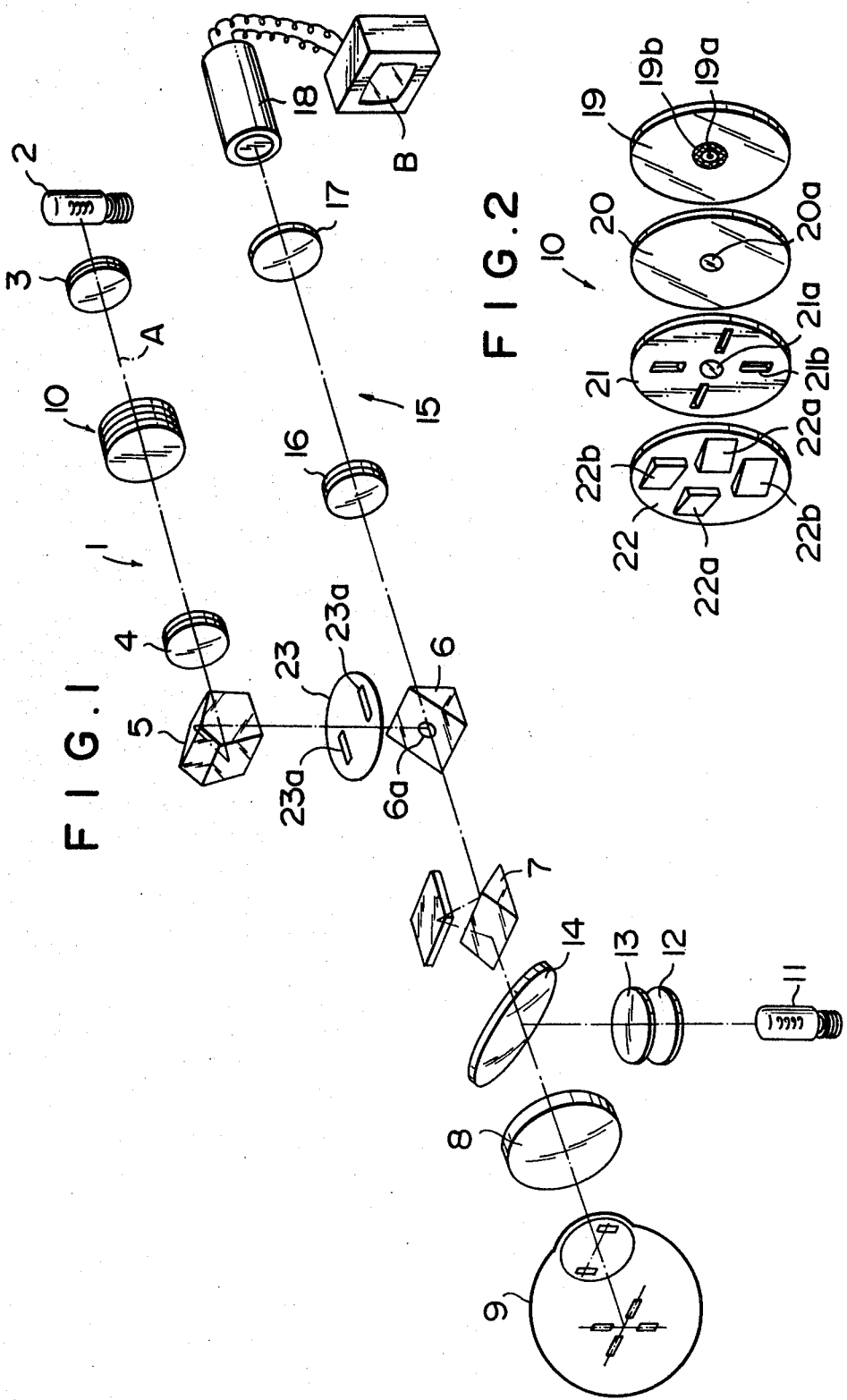

EYE REFRACTOMETER HAVING A VIEWING TARGET PROJECTING SYSTEM

The present invention relates to eye refractometers, and more particularly to eye refractometers wherein measuring targets are projected by means of infrared rays such a near infrared rays.

In eye refractometers for measuring refractive powers of patients' eye, it is required for improving measuring accuracy to maintain the patients' eyes under conditions of seeing far points. For the purpose, there is provided, in addition to the measuring target, a viewing target which is projected by a visible light. In order to maintain the patients' eyes always in conditions of seeing far points irrespective of their refractive powers, however, it is required to move the viewing target along the projecting optical axis in accordance with the refractive powers of the patients' eyes.

In conventional eye refractometers, there has been provided a viewing target projecting optical system separately from the optical system for projecting the measuring target. In order for moving the viewing target in accordance with the refractive powers of the patients' eyes, it is interconnected with the measuring target so that the former is moved in response to a movement of the latter. However, in the conventional arrangement, since the viewing target projecting optical system is provided separately from the measuring target projecting optical system, a complicated mechanism is required for such interconnection of the targets.

Proposals have already been made for projecting the viewing target coaxially with the projection of the measuring target. For example, in the measuring target projecting optical system, there may be provided a cold mirror which is transparent to infrared rays but reflects visible lights so that the visible light for projecting the viewing target is reflected by the mirror to pass along the optical axis of the measuring target projecting optical system. In this arrangement, however, inconveniencies have been encountered in that it becomes necessary to establish an exact alignment of the optical axis for the projection of the viewing target with that for the projection of the measuring target.

It is therefore an object of the present invention to provide target projecting means for infrared ray eye refractometers which does not require any complicated interconnecting mechanism between the measuring and viewing targets.

Another object of the present invention is to provide target projecting means for infrared ray eye refractometers in which the measuring and viewing targets are projected coaxially without any complicated adjustment.

According to the present invention, the above and other objects can be accomplished by an eye refractometer for measuring a refractive power of a patient's eye and comprising a target projecting optical system having an optical axis and objective lens means for projecting a measuring target by an infrared ray against the patient's eye, an observing system including means for converting a target image of the infrared ray as produced at fundus of the patient's eye into a visible image, said measuring target being provided in the projecting optical system for movement along said optical axis so that the refractive power of the patient's eye is determined from position of the measuring target when a focused target image is produced at the fundus of the patient's eye, a viewing target provided in said projecting optical system and located more distant from said objective lens means than said measuring target, filter means provided between said measuring and viewing targets and having a portion substantially corresponding to the viewing target means, said portion of the filter means being transparent to visible lights and the remainder of the filter means being transparent to an infrared ray but opaque to visible lights, said measuring and viewing targets and the filter means being connected together so that they are moved simultaneously.

In general, the measuring target is comprised of four slits which are arranged symmetrically with respect to the optical axis to form a pattern of a cross with a central blank portion in which the optical axis passes. The viewing target may then be of a circular or a ring-shaped pattern which is coaxial with the optical axis and located at a portion corresponding to the central blank portion of the measuring target. In such an arrangement, the filter means may be transparent to the visible lights only at the central portion containing the optical axis. As usual, the slits of the measuring target may be respectively associated with deflecting prisms so that the focused condition of the target image can be readily recognized.

The above and other objects and features of the present invention will become apparent from the following descriptions of a preferred embodiment taking reference to the accompanying drawings, in which;

FIG. 1 is a perspective view of the optical system of an eye refractometer embodying the features of the present invention; and, FIG. 2 is an exploded perspective view of the target assembly adopted in the optical system shown in FIG. 1.

Referring now to the drawings, particularly to FIG. 1, the optical system shown therein includes a projecting optical system 1 comprised of a lamp 2, a condenser lens 3, a projection lens 4, and a pentagonal prism 5 which directs the light through the lens 4 downwardly. Beneath the prism 5, there is provided an apertured prism 6 which has a reflecting surface for directing the light from the prism 5 forwardly. In front of the apertured prism 6, there are provided an image rotator 7 and an objective or projecting lens 8 which is adapted to be placed against a patient's eye 9. Between the lenses 3 and 4, there is provided a target assembly 10 which is movable along the optical axis A of the projecting system 1. Thus, the light from the lamp 2 is passed through the lens 3, the target assembly 10 and the lens 4 to the prism 5 where the light is reflected downwardly to the apertured prism 6. The prism 6 reflects the light forwardly and the reflected light passes through the image rotator and the projecting lens 8 to be projected to the patient's eye 9 to produce a target image at the fundus of the eye 9.

For illuminating the background, there is provided a lamp 11, a red filter 12, a condenser lens 13 and a cold mirror 14. The cold mirror 14 is located in the target projecting optical path between the image rotator 7 and the projecting lens 8. The mirror 14 is of such a type that is transparent to infrared rays but reflects visible light. Behind the apertured prism 6, there is an observing system 15 which is comprised of lenses 16 and 17 for directing and focusing the light which has passed through the aperture 6a of the prism 6. The system 15 further includes an image taking tube 18 for converting the optical image into an electrical signal so that a visible image is produced on a video display device B.

Referring now to FIG. 2, it will be noted that the target assembly 10 comprises a viewing target disc 19, a filter plate 20, a measuring target disc 21 and a deflecting prism device 22. The viewing target disc 19 is made of a generally transparent plate and has a target pattern including a central circular opaque dot 19a and an annular opaque ring 19b coaxially encircling the dot 19a. The filter plate 20 has a circular transparent portion 20a which is transparent to visible light and has a diameter substantially equal to the outer diameter of the opaque ring 19a. The remainder of the filter plate 20 is opaque to visible light but transparent to infrared ray.

The measuring target disc 21 is made of a generally opaque plate and has a central transparent portion 21a and four slits 21b which are arranged in a form of a cross. The deflecting prism device 22 includes two pairs of deflecting prisms 22a and 22b provided for cooperation with the slits 21b on the measuring target disc 21. The paired prisms 22a are inclined in diametrically opposite directions and adapted to be used for the detection of astigmatic axes. The paired prisms 22b are inclined oppositely to each other and transversely to a diametrical line so that they are used for measuring the refractive power.

The light from the lamp 2 is blocked at portions corresponding to the opaque portions 19a and 19b of the viewing target disc 19 and the light which has passed through the viewing target disc 19 is passed to the filter 20. The visible light which has passed through the transparent portion 20a of the filter 20 provides a bundle for projecting the viewing target and the remainder of the filter 20 allows only the infrared ray to pass through. The infrared ray is then passed through the slits 21b of the measuring target disc 21 to provide a light bundle for projecting the measuring target. In the illustrated arrangement, the target assembly 10 is moved along the optical axis A until a focused image of the measuring target is produced at the fundus of the patient's eye 9. As in conventional eye refractometers, the refractive power of the patient's eye 9 is determined from the position of the measuring target disc 21. Since the viewing target disc 19 is moved as unit with the measuring target disc 21, no complicated mechanism is required for interconnecting the two targets. The viewing target disc 19 is located at a more distant point from the patient's eye 9 than the measuring target disc 21, so that it is possible to maintain the patient's eye always under a condition of seeing a far point.

As illustrated in FIG. 1, the projecting optical system 1 may be provided with an aperture plate 23 which has a pair of apertures 23a located at the opposite sides of the optical axis A is substantially conjugate with the pupil of the patient's eye 9 with respect to the projecting lens 8. The apertures 23a are effective to increase the depth of the focus of the projected measuring target image.

The invention has thus been shown and described with reference to a specific embodiment, however, it should be noted that the invention is in no way limited to the details of the illustrated arrangements but changes and modifications may be made without departing from the scope of the appended claims.

I claim:

1. Eye refractometer for measuring a refractive power of a patient's eye, which comprises a target projecting optical system having an optical axis and objective lens means for projecting a measuring target by an infrared ray against the patient's eye, an observing system including means for converting a target image of the infrared ray as produced at fundus of the patient's eye into a visible image, said measuring target being provided in the projecting optical system for movement along said optical axis so that the refractive power of the patient's eye is determined from position of the measuring target when a focused target image is produced at the fundus of the patient's eye, a viewing target provided in said projecting optical system and located more distant from said objective lens means than said measuring target, filter means provided between said measuring and viewing targets and having a portion substantially corresponding to the viewing target means, said portion of the filter means being transparent to visible lights and the remainder of the filter means being transparent to an infrared ray but opaque to visible lights, said measuring and viewing targets and the filter means being connected together so that they are moved simultaneously.

2. Eye refractometer in accordance with claim 1 in which said viewing target has a pattern of a circular outer periphery and said portion of said filter means transparent to visible light is of a circular configuration having a diameter similar to that of the outer periphery of the pattern of said viewing target.

3. Eye refractometer in accordance with claim 1 in which said viewing target, said filter means and said measuring target are arranged in a coaxial relationship.

4. Eye refractometer in accordance with claim 3 in which said viewing target, said filter means and said measuring target are assembled together to move as a unit.

5. Eye refractometer in accordance with claim 3 in which said measuring target is associated with deflecting prism means.

* * * * *